(12) United States Patent
Gura

(10) Patent No.: US 11,992,590 B2
(45) Date of Patent: May 28, 2024

(54) COMBINATION WEARABLE AND STATIONARY DIALYSIS SYSTEM WITH ULTRAFILTRATE MODULE

(71) Applicant: Victor Gura, Beverly Hills, CA (US)

(72) Inventor: Victor Gura, Beverly Hills, CA (US)

( * ) Notice: Subject to any disclaimer, the term of this patent is extended or adjusted under 35 U.S.C. 154(b) by 0 days.

(21) Appl. No.: 17/333,832

(22) Filed: May 28, 2021

(65) Prior Publication Data

US 2021/0369930 A1    Dec. 2, 2021

Related U.S. Application Data

(60) Provisional application No. 63/032,272, filed on May 29, 2020.

(51) Int. Cl.
| | |
|---|---|
| A61M 1/16 | (2006.01) |
| A61M 1/26 | (2006.01) |
| A61M 1/34 | (2006.01) |

(52) U.S. Cl.
CPC ........ *A61M 1/1633* (2014.02); *A61M 1/1649* (2014.02); *A61M 1/1654* (2013.01); *A61M 1/267* (2014.02); *A61M 1/3413* (2013.01); *A61M 2202/0413* (2013.01); *A61M 2205/3334* (2013.01); *A61M 2205/502* (2013.01); *A61M 2205/75* (2013.01); *A61M 2205/8206* (2013.01); *A61M 2209/088* (2013.01)

(58) Field of Classification Search
None
See application file for complete search history.

(56) References Cited

U.S. PATENT DOCUMENTS

| | | | |
|---|---|---|---|
| 6,406,631 B1 | 6/2002 | Collins et al. | |
| 10,933,183 B2 | 3/2021 | Gura et al. | |
| 2004/0068219 A1 | 4/2004 | Summerton et al. | |
| 2006/0241543 A1 | 10/2006 | Gura | |
| 2008/0217245 A1 | 9/2008 | Rambod et al. | |
| 2009/0120864 A1* | 5/2009 | Fulkerson | A61M 1/3607 210/321.71 |
| 2011/0184340 A1 | 7/2011 | Tan et al. | |
| 2013/0213890 A1* | 8/2013 | Kelly | A61M 1/1696 210/101 |

(Continued)

FOREIGN PATENT DOCUMENTS

| | | |
|---|---|---|
| IN | 202217074529 A | 10/2023 |
| KR | 20150070922 | 6/2015 |
| WO | WO-2021243200 A1 | 12/2021 |

OTHER PUBLICATIONS

"International Application Serial No. PCT/US2021/034844, International Search Report dated Sep. 23, 2021", 4 pgs.

(Continued)

*Primary Examiner* — Krishnan S Menon
(74) *Attorney, Agent, or Firm* — Wilson Sonsini Goodrich & Rosati

(57) ABSTRACT

The present disclosure includes systems and methods for hemodialysis, such as including a first dialysis module and an auxiliary module detachably connectable to the first dialysis module. The first dialysis module can include a dialyzer, a blood circuit, a dialysate circuit, and a sorbent. The auxiliary module can include an ultrafiltrate collector operably couplable to the dialysate circuit for removing excess fluid therefrom.

19 Claims, 11 Drawing Sheets

(56) References Cited

U.S. PATENT DOCUMENTS

2018/0250461 A1    9/2018    Gura

OTHER PUBLICATIONS

"International Application Serial No. PCT/US2021/034844, Written Opinion dated Sep. 23, 2021", 4 pgs.
"International Application Serial No. PCT/US2021/034844, International Preliminary Report on Patentability dated Dec. 8, 2022", 6 pgs.
"European Application Serial No. 21812822.1, Extended European Search Report dated Oct. 16, 2023", 7 pgs.

* cited by examiner

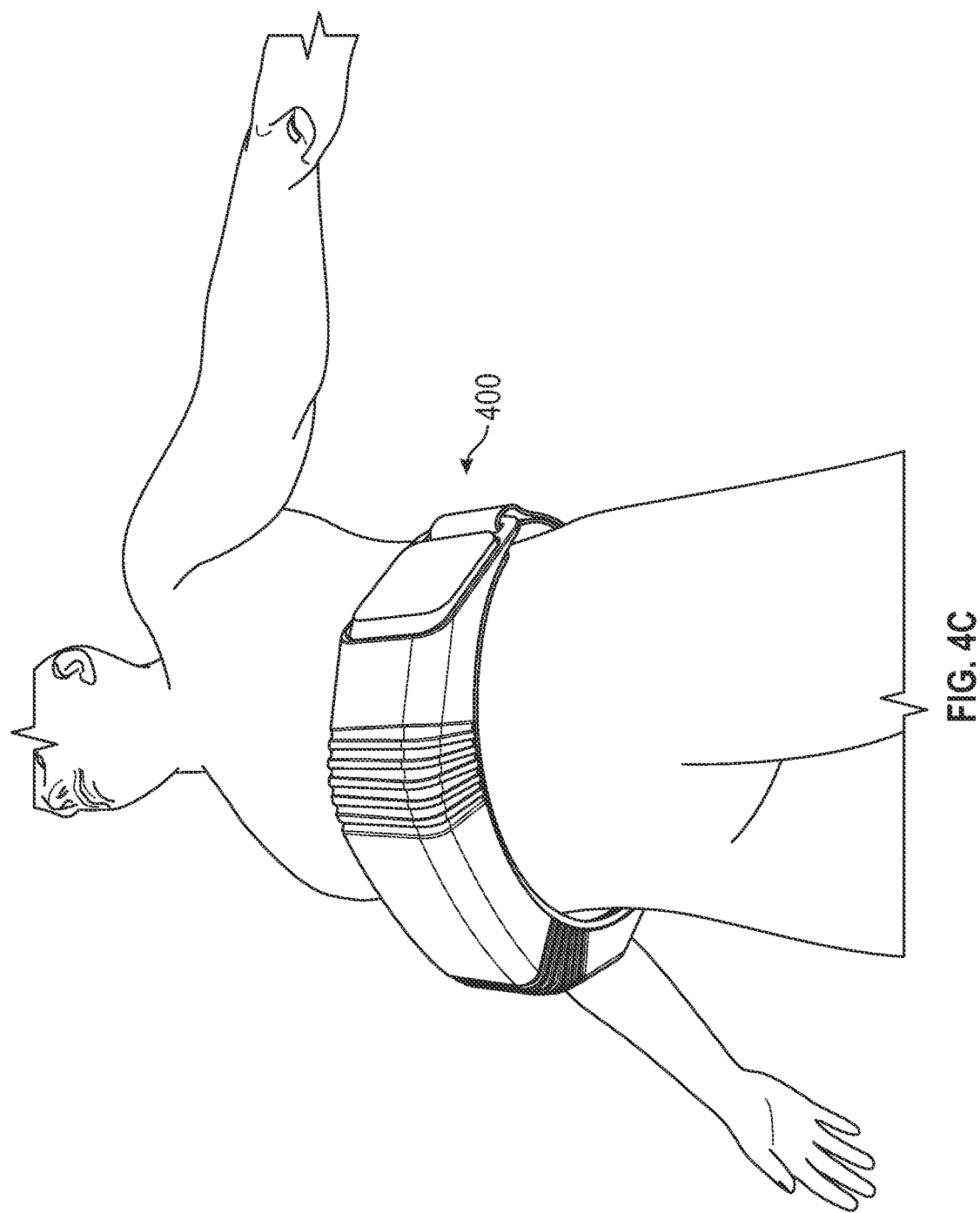

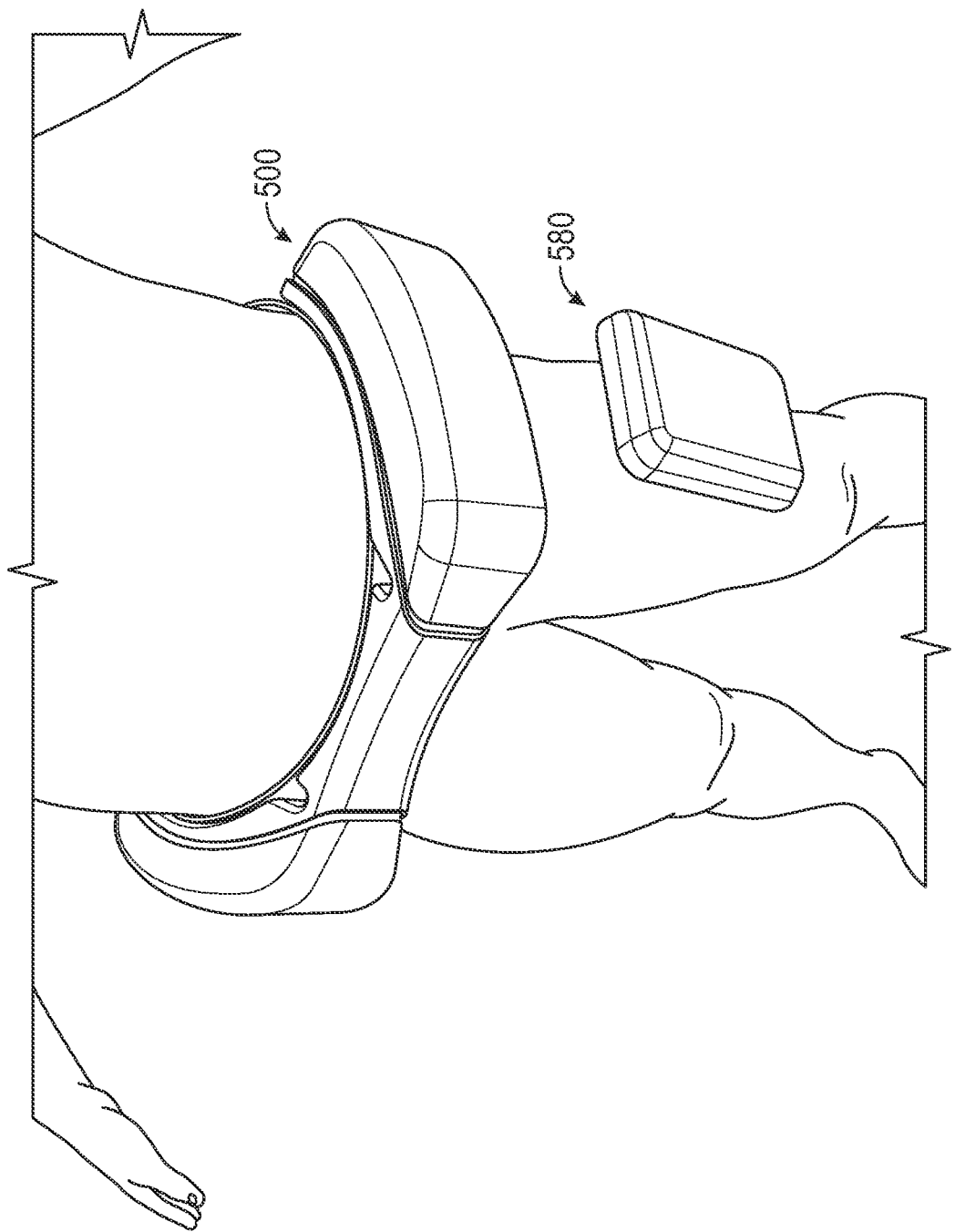

COMBINATION WEARABLE AND STATIONARY DIALYSIS SYSTEM WITH ULTRAFILTRATE MODULE

CROSS-REFERENCE TO RELATED APPLICATION

This patent application claims the benefit of U.S. Provisional Patent Application No. 63/032,272, filed May 29, 2020, entitled "COMBINATION WEARABLE AND STATIONARY DIALYSIS SYSTEM WITH ULTRAFILTRATE MODULE", which is incorporated by reference herein in its entirety.

BACKGROUND

Hemodialysis can be a renal replacement therapy used by patients who have end stage renal disease (ESRD). These patients can no longer rely upon their kidneys to provide desired removal of waste from the blood. Hemodialysis can involve extracorporeal removal of toxins from a patient's blood using a dialyzer, where the toxins diffuse across a semipermeable membrane in the dialyzer to a dialysate solution due to a concentration gradient across the membrane.

SUMMARY OF THE DISCLOSURE

Additional aspects and advantages of the present disclosure will become readily apparent to those skilled in this art from the following detailed description, wherein only some examples of the present disclosure are shown and described, simply by way of illustration of the several modes or best mode contemplated for carrying out the present disclosure. As will be realized, the present disclosure is capable of other and different examples, and its several details are capable of modifications in various obvious respects, all without departing from the disclosure. Accordingly, the drawings and description are to be regarded as illustrative in nature, and not as restrictive.

In an example, a system for hemodialysis can include a first dialysis module and an auxiliary module detachably connectable to the first dialysis module. The first dialysis module can include a dialyzer, a blood circuit configured to receive blood from a patient, circulate the blood through the dialyzer, and return cleaned blood to the patient, a dialysate circuit configured to circulate dialysate through the dialyzer and remove impurities from the blood and a first sorbent for removing toxins from the blood. The auxiliary module can include a pump connectable to the dialyzer for pumping the dialysate through the dialysate circuit and a filter configured to remove fluid from the system, the filter fluidly coupled to the pump and the dialysate circuit.

In an example, a method of hemodialysis can include continuously removing toxins from blood with a portable dialysis module situated on the patient's body and selectively removing excess fluid from the portable dialysis module by connecting the portable dialysis module to a detachable auxiliary module comprising an ultrafiltrate collector.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various examples discussed in the present document.

FIGS. 4A-4C are perspective views of a portable daytime hemodialysis system in an example.

FIGS. 5A-5C are perspective views of a portable daytime hemodialysis system in an example.

DETAILED DESCRIPTION

Figure 1:
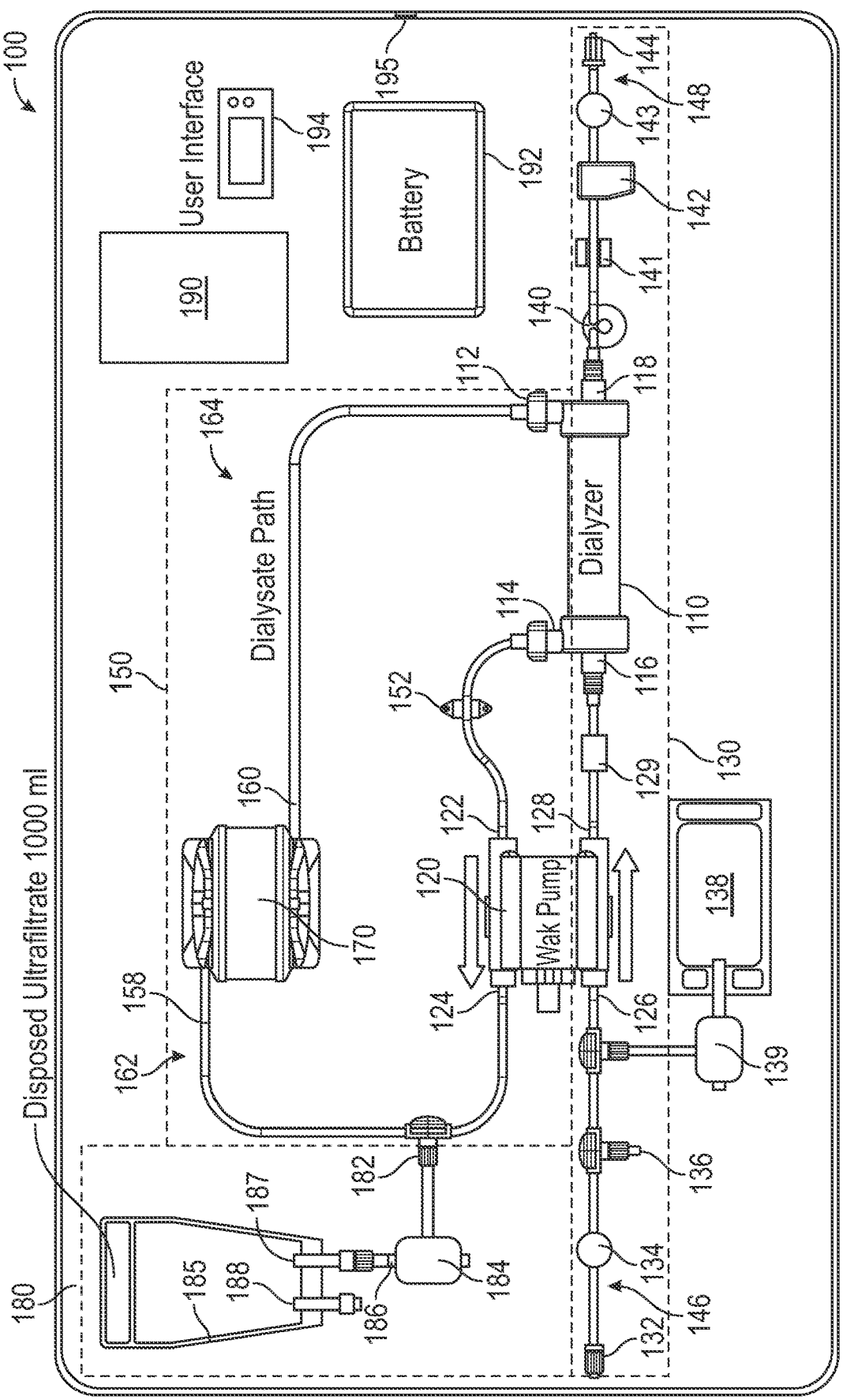
FIG. 1 is a schematic diagram of a portable daytime hemodialysis system with a detachable auxiliary pump module in an example.

While some examples of the invention have been shown and described herein, it will be obvious to those skilled in the art that such illustrations are provided by way of example only. Numerous variations, changes, and substitutions will now occur to those skilled in the art without departing from the invention. It should be understood that various alternatives to the examples of the invention described herein may be employed in practicing the invention.

Disclosed is a system and methods of hemodialysis. The system includes a portable daytime module that can be comfortably worn by the patient during normal daytime activity. The daytime module can plug into a stationary nighttime module having additional sorbents, such as for removal of urea. The daytime and nighttime modules can share a pump, dialysate circuit, and blood circuit. The system has a detachable auxiliary pump and ultrafiltrate module to allow for improved portability of the daytime module.

Hemodialysis, commonly called kidney dialysis or simply dialysis, is a process of purifying the blood of a person whose kidneys are not working normally. This type of dialysis achieves the extracorporeal removal of waste products such as creatinine and urea and free water from the blood when the kidneys are in a state of kidney failure. Hemodialysis can be an outpatient or inpatient therapy. Routine hemodialysis is conducted in a dialysis outpatient facility, either in a purpose built room in a hospital or a dedicated, stand-alone clinic, or at home. Less frequently hemodialysis is done at home. Dialysis treatments in a clinic are initiated and managed by specialized staff made up of nurses and technicians; dialysis treatments at home can be self-initiated and managed or done jointly with the assistance of a trained helper.

Conventional hemodialysis has a number of disadvantages, such as restricted independence, as people undergoing this procedure cannot travel around because of supplies' availability and being tethered to a large stationary device during treatment; requires high water quality; a large quantity of water; and continuous source of electricity, typically provided by a power plug connected to an outlet; requires reliable technology like dialysis machines; requires care givers having more knowledge of the complicated procedure and equipment; requires ongoing and repetitive time to set up and clean dialysis machines.

Additionally, hemodialysis often involves fluid removal through ultrafiltration, as most patients with renal failure pass little or no urine. Side effects caused by removing too much fluid or removing fluid too rapidly can include low blood pressure, fatigue, chest pains, leg-cramps, nausea and headaches. These symptoms can occur during the treatment and can persist post treatment; they are sometimes collectively referred to as "dialysis hangover" or "dialysis washout." The severity of these symptoms is usually proportionate to the amount and speed of fluid removal. However, the impact of a given amount or rate of fluid removal can vary greatly from person to person and day to day.

Conventional hemodialysis is usually done three times per week, for about 3-4 hours for each treatment, during which the patient's blood is drawn out through a tube at a rate of 200-400 mL/min. The tube is connected to a 15, 16, or 17 gauge needle inserted in the dialysis fistula or graft, or connected to one port of a dialysis catheter. The blood is then pumped through the dialyzer, and then the processed blood is pumped back into the patient's bloodstream. Optionally in any example, the blood can be pumped to the patient through another tube connected to a second needle or port. Optionally in any example, the blood can be pumped to the patient through a dual lumen catheter at the same location where blood is removed from the body, such as to allow one access point to the body to both remove and return blood in two separate lumens.

During the procedure, the patient's blood pressure is closely monitored, and if it becomes low, or the patient develops any other signs of low blood volume such as nausea, the dialysis attendant can administer extra fluid through the machine. During the treatment, the patient's entire blood volume (about 5000 cc) circulates through the machine every 15 minutes. During this process, the dialysis patient is exposed to a week's worth of water for the average person. Daily hemodialysis is typically used by those patients who do their own dialysis at home. It is less stressful (more gentle) but does require more frequent access. Daily hemodialysis is commonly done for 2 hours six days a week. The procedure of nocturnal hemodialysis is similar to conventional hemodialysis except it is typically performed three to six nights a week and between six and ten hours per session while the patient sleeps.

Described herein are systems and methods related to a dialysis system which can include both a first dialysis module which performs dialysis functions during a period when the patient desires to be mobile, such as during the daytime, and a second dialysis module configured to perform dialysis functions during a period of time when mobility is not as important to the patient, such as during the nighttime. The system can also include a detachable auxiliary module for collection of ultrafiltrate and liquid removal.

The patient can alternate use of the first dialysis modules alone, and the second dialysis module in conjunction with the first dialysis module, such as during a 24-hour period. The patient can selectively attach or detach the auxiliary module to allow for removal of fluid at various parts of the day or attach the auxiliary module for an extended period of time when stationary.

The first dialysis module can be worn by the patients, such as under their clothes. The first dialysis module is lightweight and/or compact to facilitate transport of the system such that patients can maintain activities of daily life. The removal or addition of the auxiliary module with an ultrafiltrate collector can allow even more patient movement and mobility during the day.

Meanwhile, the second dialysis module connects into the first dialysis module to create a stationary dialysis system, configurable to provide additional toxin removal functions. The stationary dialysis system is stationary, for example being configured to be positioned on a support. This can allow a patient to be mobile during the day while maintaining overall desired removal of toxins.

FIG. 1 is a schematic diagram of a portable daytime first dialysis module 100 with a detachable auxiliary pump module 180. The portable daytime hemodialysis system ("first dialysis module") 100 can be configurable to be transported by a patient, for example to perform toxin removal functions while a patient is mobile, such as during the daytime. The first dialysis module 100 can be lightweight and compact in size to provide desired patient mobility. For example, the first dialysis system can be of a weight less than 5 lbs., less than 4 lbs., less than 3 lbs., less than 2.5 lbs., less than 2 lbs., less than 1.5 lbs., or less than 1 lb. The first dialysis module 100 can be configurable to be worn by the patient while the patient is going about his or her daily business without requiring tethering to external power sources or external components. For example, the first dialysis module 100 can be a wearable artificial kidney. The first dialysis module 100 can be coupled to a belt such that the first dialysis module 100 is worn by the patient. The first dialysis module 100 can be worn by the patient, but otherwise untethered.

The first dialysis module 100 can include a dialyzer 110, a pump 120, a blood circuit 130, a dialysate circuit 150, a sorbent cartridge 170, auxiliary module 180, control unit 190, power source 192, user interface 194, and power jack 195.

The dialyzer 110 can have a dialysate input 112, a dialysate output 114, a blood inlet 116, and a blood outlet 118. Dialysate can flow through the dialyzer 110 in a first direction while the blood flows through the dialyzer 110 in a counter current flow. Counter current flow can maximize the gradient between the dialysate circuit 150 and the blood circuit 130, therefore maximizing exchange across the dialyzer 110 membrane. Toxins from the blood flow can diffuse into the dialysate across semi-porous membranes of the dialyzer 110 as the blood and dialysate flow across opposing surfaces of the semi-porous membranes. In an example, blood flow can travel in a clockwise fashion through the blood circuit 130, while the dialysate can flow in a counterclockwise fashion through the dialysate circuit 150.

In dialysis systems, some toxins be removed at a steady rate over a 24-hour period, but generally not faster. However, some toxins can be removed over shorter periods of time without negative consequences to the patient. There are two types of toxins: those bound to protein; and free toxins. Free toxins are generally considered to be more toxic. Examples of toxins that require removal over 24 hours include p-cresyl and indoxyl sulfate. These are part of a group of toxins called protein bound toxins (P-BUTS). The free form, which is the only toxic one, comes out in the urine, keeping its level low in a healthy patient. In dialysis the free fraction comes out on dialysis and the level of the free toxin is also low, however, as soon as the patient is on a dialysis machine, the protein bound toxins re-equilibrate with the free fraction, that comes up again to toxic levels. There are about 25 known P-BUTS. The first dialysis module 100 can be configured to remove toxins at a steady rate over a 24-hour period.

The pump 120 can have a dialysate input 122, a dialysate output 124, a blood inlet 126, and a blood outlet 128. The pump 120 can be a side-to-side pulsatile pump. The side-to-side pulsatile pump 120 can be powered by a battery, including a rechargeable battery, and/or by an electrical wall outlet. For example, the side-to-side pulsatile pump 120 can be powered by a battery to enable transport of the pump 120, thereby facilitating transport of the dialysis system which incorporates the pump 120, such as first dialysis module 100. An example of such a side-to-side pump is disclosed in U.S. patent application Ser. No. 15/890,718; the entire contents of which are incorporated herein by reference.

The side-to-side pulsatile pump 120 can be configured to retain a blood tubing permitting the flow of blood therethrough from the patient, and a dialysate tubing permitting flow therethrough of dialysate, within a pump casing. The pump can include a compression disc configured to provide side-to-side motion to apply a first pressure to the blood ventricle tubing and a second pressure to the dialysate ventricle tubing in alternate fashion. This can allow for alternating pumping of the blood circuit 130 and the dialysate circuit 150. In some cases, the pump can be driven by a motor and gear box. The pump 120 can create a pulsatile flow where the blood pulses are out of phase with the dialysate pulses, such that, for example, the peak of the blood pulse is 90 to 180 degrees out of phase with the peak of the dialysate flow.

One or more side-to-side pulsatile pumps described herein can be configured to provide desired pumping volume for both blood and dialysate, while reducing or eliminating problems associated with known pumps. Optionally in any example, one or more side-to-side pulsatile pumps described herein can provide pumping volumes of greater than about 35 milliliter per minute (mL/min). Optionally in any example, a dialysis system using a side-to-side pulsatile pump can provide a flow rate of dialysate of about 100 mL/min.

The blood circuit 130 can have an inlet 132, a flow control element 134, a saline flush 136, a blood thinner hookup 138 with pump 139, a bubble filter 140, a bubble detector 141, a flow sensor 142, a flow control element 143, and an outlet 144. The blood circuit can contain first portion 146 and second portion 148. The first portion contains undialyzed blood, the second portion contains dialyzed blood. The blood circuit 130 can, for example, be made of tubing or other conduit suitable for flow of blood. The flow control elements 134, 143, can be elements such as valves, clamps, or other elements that allow for turning off and on blood flow, or otherwise controlling flow rates through the blood circuit 130.

In the first portion 146 of the blood circuit 130, the inlet 132 can be configured for attachment to a patient. In some cases, the inlet 132 can be a blood thinner infusion inlet, such as for adding blood thinner to the blood flow to prevent blood clots from forming within the blood circuit 130 of the first dialysis module 100. In some cases, such as shown in first dialysis module 100, the blood thinner hookup 138 can be separate from the inlet. Such a hookup can be connected to a blood thinner reservoir (not shown). Example blood thinners can include heparin, or more specifically, low molecular weight heparins, direct thrombin inhibitors, danaparoid, ancrod, r-hirudin, abciximab, tirofiban and argatroban, among others known to those skilled in the art. Optionally in any example, a blood thinner infusion inlet can be positioned elsewhere on the blood circuit 130, such as after the pump 120. The infusion of one or more blood thinners into the blood circuit 130 can be actuated, for example, by the pump 139.

The first portion 146 can include flow of blood from the patient that has not yet been treated for toxins. The second portion 148 can include flow of blood back to the patient that has been treated for toxins. In the first portion 146, the blood circuit 130 can allow for flow of blood from the inlet 132 through the pump 120 to the dialyzer 110 via blood inlet 116, where toxins can be removed. In the second portion 148, upon exiting the dialyzer at blood outlet 118, blood can flow towards the outlet 144 towards the patient. The blood flow can run through a number of optional components which may be included in any example, such as the bubble filter 140 and bubble detector 141, the flow sensor 142, or other sensors or filters.

The bubble filter 140 and bubble detector 141 can be in fluid communication with the blood flow exiting the dialyzer 110 such that presence of air bubbles within the blood is detected and communicated to the control unit 190. The control unit 190 is configurable to pause and/or power off the first dialysis module 100 upon detection of air bubbles within the blood flow.

The flow sensor 142 can be in line or parallel to the blood circuit 130, such as in second portion 148 of the blood circuit. The flow sensor 142 can be configured to measure the rate at which blood is flowing through the first dialysis module 100. Optionally in any example, one or more flow sensors can be alternatively or additionally be on the dialysate circuit for measuring flow of dialysate. The flow sensor 142 can be a mechanical flow meter, a pressure-based flow meter, a variable area flow meter, an optical flow meter, combinations thereof, or other type of flow sensors.

The flow sensor 142 on the blood circuit 130 can detect the volume of blood moving through the blood circuit over a given time period. This information can be communicated to the control unit 190, which is turn can monitor the flow of blood through the circuit. If the blood flow is outside of a normal range, the control unit 190 can alter the movement of the dialyzer 110 and pump 120 to change the flow of blood and/or dialysate through the module 100. For example, if the blood flow is too slow, it may indicate a clot or blockage, which may need to be addressed. Optionally in any example, a change in flow may trigger an alarm such as an audible, visual, tactile, or other indicia to the user. If the blood flow is too quick, the control unit 190 can slow the mechanism of the pump 120 to modulate the flow of fluid in the module 100 accordingly.

Optionally in any example, the first dialysis module 100 can additionally include a pH sensor 129 tied to the control unit 190 such as to test for ammonia in the blood circuit. The pH sensor 129 can be, for example, positioned between the dialyzer 110 and the outlet 144. Since ammonia is such a strong base, the pH sensor 129 can provide a safety mechanism to detect when the sorbent cartridges are no longer effective for removing ammonia from the system. The optional pH 129 sensor can be in fluid communication with the blood flow exiting the dialyzer 110 such that the presence of ammonia within the fluid is detected and communicated to the control unit 190. The control unit 190 can be configurable to pause and/or power off the first dialysis module 100 upon detection of ammonia within the blood flow, or otherwise trigger an alarm. The pH sensors 129 can be, for example, a combination pH sensor, a differential sensor, a laboratory sensor, a process pH sensor, or other type of pH sensor.

The dialysate circuit 150 can include a blood detector 152 and connections 158, 160 to the sorbent cartridge 170. The dialysate circuit can include first portion 162 and second portion 164. The dialysate circuit 150 is a sterile dialysate circuit for flow of dialysate therethrough. The dialysate circuit 150 can allow flow of a dialysate through the dialyzer 110 and the pump 120, through the sorbent cartridge 170, and back to the dialyzer 110. The dialysate circuit 150 can, for example, be made of tubing or other conduit suitable for flow of dialysate.

The first portion 162 of the dialysate circuit 150 can include a blood detection access port connecting the dialysate circuit 150 to the blood detector 152. The blood detection access port can be coupled the blood detector 152, such that presence of blood in the dialysate exiting the dialyzer 110 can be detected. In some cases, breakage in the membranes of the dialyzer 110 can result in blood entering the dialysate flow. The blood detector 152 can be in communication with the control unit 190 such that the control unit 190 will pause and/or power off the first dialysis module 100 upon detection of blood in the dialysate, or otherwise cause an alarm to be initiated to the user.

Dialysate can be driven by the pump 120 from the dialyzer 110 through dialysate output 114 into the first portion 162 of the dialysate circuit towards the sorbent cartridge 170 via connection 158. In some cases, the first portion 162 of the dialysate circuit can be connected to the auxiliary module 180. The dialysate can be driven through the sorbent cartridge 170, where the sorbent treats the dialysate, and then the dialysate flows out the connection 160 to the second portion 164 of the dialysate circuit. In the second portion 164 of the dialysate circuit, the dialysate can be driven from the sorbent cartridge 170 back towards the dialyzer, where the dialysate can enter the dialyzer 110 through the dialysate input 112.

In first dialysis module 100, which is designed to be mobile, one lighter weight sorbent cartridge 170 can be used. The sorbent cartridge 170 can be, for example, charcoal. Optionally in any example, the sorbent cartridge 170 can be configured to remove one or more of organic uremic metabolites and heavy metals. Optionally in any example, the sorbent cartridge 170 is configured to remove one or more of creatinine, uric acid and P2 micro globulins, p-cresol, indoleacetic acid and hippurate. The sorbent cartridge 170 comprises activated carbon, such as charcoal. The dialysate exiting the sorbent cartridge 170 is regenerated dialysate, such that dialysate entering the dialyzer 110 is cleaned dialysate.

The auxiliary module 180 can be a detachable module for removal of ultrafiltrate. In some cases, the first portion 162 of the dialysate circuit can be connected to the auxiliary module 180 through the ultrafiltrate outlet port 182. The ultrafiltrate outlet port 182 can be, for example, a spike for fluid-tight connection and detachment of the auxiliary module 180 as desired. The auxiliary module 180 can include ultrafiltrate outlet port 182, a pump 184, and an ultrafiltrate collector 185.

The auxiliary module 180 can be removeable or attachable to the first dialysis module 100, using a connector element. The connector element can be on the auxiliary module 180, and releasably connect with a cooperating connector element on the first dialysis system. For example, a surgical spike could also be on the auxiliary module 180, and the first dialysis module 100 can have a receptacle such as a resilient rubber seal for receiving the spike. In some cases, the connector, such as a surgical spike, can be located on the first dialysis module 100 and the cooperating connector is located on the auxiliary module.

The ultrafiltrate from the dialysate can exit the dialysate circuit 150 through the ultrafiltrate outlet port 182 and can be collected within the ultrafiltrate collector 185 which can be a bag, cannister or any other reservoir for collecting the ultrafiltrate. The ultrafiltrate collector 185 can include an ultrafiltrate inlet port 186 configured to be coupled a first fluid channel 187. The first fluid channel 187 can be configured to provide fluid communication between the ultrafiltrate pump 184 and the ultrafiltrate collector 185. A second fluid channel 188 can be coupled to the ultrafiltrate pump 184 to provide fluid communication between the ultrafiltrate pump 184 and the dialysate circuit 150. The ultrafiltrate pump 184 can be used to control flow of ultrafiltrate from the dialysate circuit 150 into the ultrafiltrate collector 185. The ultrafiltrate pump 184 can be a micro-pump. Removal of ultrafiltrate can provide removal of water and sodium from the dialysate. For example, the ultrafiltrate removal rate can be maintained at a physiological rate in order to reduce or avoid blunt hemodynamic changes.

Optionally in any example, the dialysate circuit 150 of the first dialysis module 100 can include one or more points at which optional electrolyte is infusible into the dialysate flow. One or more types of optional electrolyte solutions can be added into the dialysate flow to facilitate maintaining electrolyte homeostasis. For example, one or more of optional electrolyte supplement solutions, such as electrolyte supplement solutions comprising sodium bicarbonate, calcium, and/or magnesium, can be infused into the dialysate flow at one or more optional electrolyte infusion points.

Optionally in any example, the second portion 164 of the dialysate circuit can include one or more electrolyte infusion ports with electrolyte reservoirs (not shown). The electrolyte reservoir can retain an electrolyte solution. Optionally in any example, the electrolyte solution can be used to adjust the pH of the dialysate. The electrolyte solution can be, for examples, sodium bicarbonate solution. The electrolyte solution can be infused into the dialysate flow via an electrolyte infusion port. Flow of the electrolyte solution into the dialysate flow can controlled by an electrolyte solution pump. Such an electrolyte solution pump can be configured to pump up to about 5 milliliters per hour (mL/hr), or for example from about 1 mL/hr to about 2 mL/hr, up to about 5 mL/hr.

The control unit 190 can be in electrical communication with one or more components of the first dialysis module 100. For example, the control unit 190 can be in communication with the bubble detector 141 and the blood detector 152 such that an alarm is initiated when air bubbles are detected in the blood flow and/or blood is detected in the dialysate flow. Optionally in any example, the control unit 190 is configured to pause and/or power down the first dialysis module 100 upon detection of air bubbles in the blood flow and/or blood in the dialysate flow. Optionally in any example, the control unit 190 is configured to control the pump 120 to provide desired flow of blood and/or dialysate through the first dialysis module 100. The control unit 190 can control one or more optional pumps configured to control flow of electrolyte into the dialysate, blood thinner into the blood flow, and/or ultrafiltrate from the dialysate.

The power source 192 can be a portable power source, such as a battery or a rechargeable battery, connected to the first dialysis module 100. In some cases, the power source 192 can additionally include an option to plug into a wall outlet.

The user interface 194 can allow for the patient to see status updates or monitor functioning of the dialysis first dialysis module 100. The user interface 194 can include, for example, buttons, a screen, lights, or other indicia that can convey whether the system is functioning properly.

The first dialysis module 100 is lightweight and wearable by a patient during the daytime, or when he or she is going about normal daily activities. The first dialysis module 100 can be worn, for example, as a belt, shown and discussed with reference to FIGS. 3A-3B, 4A-4C, and 5A-5C below. The light-weight first dialysis module 100 can include an activated carbon cartridge configured to adsorb various toxins from the dialysate. The activated carbon is configured to remove one or more of creatinine and β2 micro globulins, p-cresol, indoleacetic acid, hippurate, and heavy metals, from the dialysate. Optionally in any example, the first dialysis module is not configured to remove urea from the blood flow. In the first dialysis module alone, worn in a mobile configuration, a charcoal sorbent, or other sorbents known in the art, can continuously removes the free fraction of the P-BUTS over 24 hours.

The detachable auxiliary module 180 can allow for a light weight and comfortable system with flexibility for regular, but not necessarily continuous, removal of sodium and water. The patient can strategically and selectively plug into the auxiliary module 180 as needed to expel fluid. This can be monitored and timed according to the patient's needs to avoid hemodynamic problems.

The first dialysis module 100 and the auxiliary module 180 can be combined with the second dialysis module 200 to allow for removal of additional toxins over a shortened, stationary, period of time.

Figure 2:
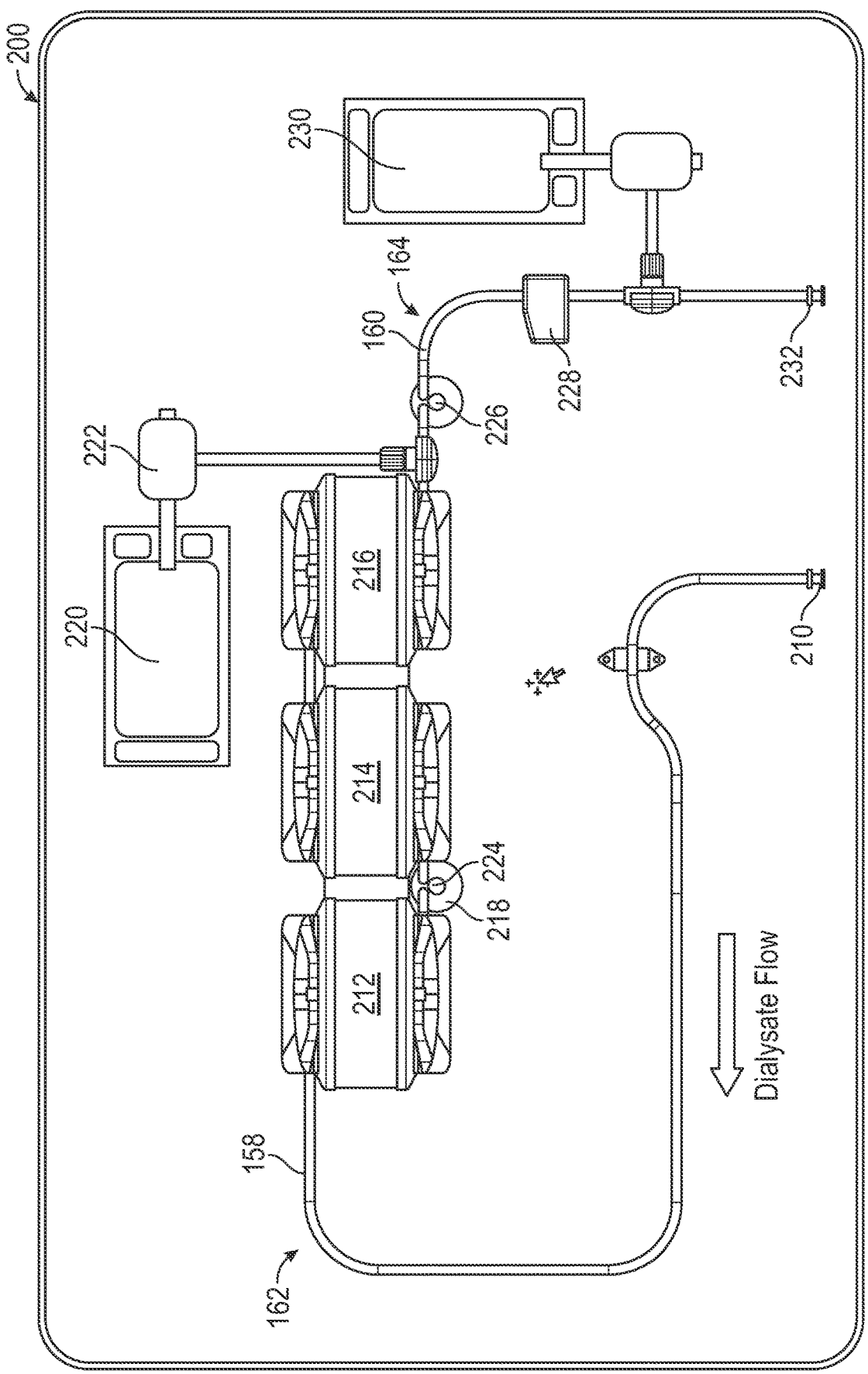
FIG. 2 is a schematic of a stationary nighttime hemodialysis module for use with a daytime hemodialysis system, in an example.

FIG. 2 is a schematic of a stationary nighttime hemodialysis module 200 for use with a daytime first dialysis module 100, shown in FIG. 1. The stationary nighttime hemodialysis module ("second dialysis module") 200 can include a dialysate inlet 210, sorbents 212, 214, 216, ammonia sensor 218, first electrolyte module 220 with pump 222, bubble filters 224, 226, flow sensor 228, second electrolyte module 230, and dialysate outlet 232.

The second dialysis module 200 is a module that plugs into the first dialysis module 100 of FIG. 1. The second dialysis module 200 does not perform hemodialysis alone. Instead, the dialysate inlet 210 and the dialysate outlet 232 are connected to the connections 158, 160 of the dialysate circuit 150 of the first dialysis module 100. This replaces the sorbent cartridge 170 from the daytime first dialysis module 100 with the sorbent cartridges 212, 214, and 216 from the second dialysis module 200. Optionally in any examples, the sorbent cartridge 170 from system 100 can be used with the second dialysis module 200 instead of one of the sorbent cartridges 212, 214, 216.

When the second dialysis module 200 is plugged into the first dialysis module 100 for use by the patient, the dialysate can travel from the dialyzer 110 into the first portion 162 of the dialysate circuit 150, through the blood detector 152, through the pump 120, up past the auxiliary module 180, and into the dialysate inlet 210 of the second dialysis module 200. Optionally in any examples, the first dialysis module can recharge while plugged into the second dialysis module.

The dialysate can then be driven, by the pump 120, through the second dialysis module 200, from the dialysate inlet 210 through sorbent cartridges 212, 214, 216 in sequence. The dialysate can travel through one or more of bubble filters 224, 226, ammonia sensor 218, and flow sensor 228, in addition to auxiliary electrolyte modules 220, 230, on its way to the dialysate outlet 232. Once the dialysate reaches the dialysate outlet 232 of the second dialysis module 200, it can be driven back into the dialyzer 110.

The second dialysis module can include a plurality of types of sorbent materials configured to regenerate the dialysate. For example, the second dialysis can include a plurality of sorbent cartridges to provide a plurality of types of sorbent materials. A patient can alternate use of the first dialysis module and a second dialysis module, for example for about 12 hours each during a 24 hour period, such that the patient remains mobile during the day while maintaining overall desired removal of toxins.

A sorbent material in the one or more sorbent cartridges 212, 214, 216 can include sorbents such as carbon, charcoal, zirconium phosphate; hydrous zirconium oxide; metals or alloys containing zirconium; an organic and/or inorganic compound comprising zirconium; minerals comprising zirconium; or urease.

The sorbent cartridges 212, 214, 216, can include a urea converter cartridge 212 and two other sorbent cartridges 214, 216. The urea converter cartridge 212 can be configured to convert urea to ammonium carbonate, which in the presence of hydrogen ions generates carbon dioxide. For example, the urea converter cartridge can include urease. Optionally in any example, the urea converter cartridge 212 comprises one or more sorbent materials configured to adsorb toxins in the dialysate. The one or more sorbent materials can be configurable to adsorb ammonium, such as the ammonium generated by the degradation of urea into ammonium carbonate. Optionally in any example, the one or more sorbent materials are configurable to adsorb other cations, including cations of calcium, magnesium, and/or potassium. Optionally in any example, the urea converter cartridge 212 includes zirconium phosphate. For example, zirconium phosphate in the urea converter cartridge 212 can remove ammonium from the dialysate, along with calcium, magnesium and potassium cations, while releasing sodium and hydrogen ions.

Optionally in any example, the urea converter cartridge 212 comprises more than one distinct cartridge and/or distinct portions of cartridges. Optionally in any example, the urea converter cartridge 212 is configurable to be split into more than one distinct cartridge. The urea converter cartridge 212 can include one or more cartridges to retain the urea converter component, such as the urease, and one or more cartridges to retain the one or more sorbent materials. For example, the urea converter cartridge 212 can include a first cartridge configured to retain the urease and a second cartridge configured to retain the one or more sorbent materials. Optionally in any example, the urea converter cartridge 212 comprises more than one distinct portions, with one or more respective portions comprising the urease and one or more sorbent materials.

The first sorbent cartridge 214 can be configurable to remove one or more heavy metals and/or one or more anions from the dialysate. For example, the first sorbent cartridge 214 can remove one or more of iron, mercury and aluminum. In some cases, the first sorbent cartridge 214 is configured to remove one or more phosphate and sulfide anions. In some cases, the first sorbent cartridge 214 comprises hydrous zirconium oxide. For example, dialysate can flow through the urea converter cartridge 212 and into the first sorbent cartridge 214 where heavy metals, such as iron, mercury and aluminum, and phosphate and sulfide anions are removed from the dialysate, in exchange for acetate. Zirconium hydroxide binds phosphate and releases acetate, bicarbonate and sodium in small amounts. Zirconium phosphate removes ammonium, calcium, magnesium and potassium.

The second sorbent cartridge 216 can be configurable to remove one or more of organic uremic metabolites and heavy metals. In some cases, the second sorbent cartridge 216 is configured to remove one or more of creatinine, uric acid and β2 micro globulins, p-cresol, indoleacetic acid and hippurate. The second sorbent cartridge 216 can include activated carbon, such as charcoal. In some cases, the second sorbent cartridge 216 has characteristics similar to or the same as the sorbent cartridge 170 described with reference to FIG. 1.

Once the dialysate flows through the sorbent containing cartridges 212, 214, 216, the dialysate can be driven back through the second dialysis module 200 past the ammonia sensor 218, the first electrolyte module 220, the bubble filters 224, 226, the flow sensor 228, the second auxiliary module 230, and to the dialysate outlet 232, where the cleaned dialysate can return to the dialyzer 110. The dialysate exiting the sorbent cartridges 212, 214, 216 is regenerated dialysate, such that dialysate flowing into the dialyzer 110 is cleaned dialysate which can be used to remove toxins from the blood of the patient. Since the dialysate system is sterile, ideally, the dialysate would be changed between each conversion from the first dialysis module 100, to the second dialysis module 200, or between each conversion from the second dialysis module 200, to the first dialysis module 100.

The second dialysis module 200 can have one or more ammonia sensors 218 in line with the dialysate circuit. The ammonia sensor 218 can be, for example, a pH sensor similar to the pH sensor of first dialysis module 100. The ammonia sensor can be tied to the control unit 190 to test for ammonia in the blood circuit. Since ammonia is such a strong base, the optional pH sensor provides a safety mechanism to detect when the sorbent cartridges are no longer effective for removing ammonia from the system. The optional pH sensor is in fluid communication with the blood flow exiting the dialyzer 110 such that the presence of ammonia within the fluid is detected and communicated to the control unit 190. The control unit 190 can be configurable to pause and/or power off the first dialysis module 100 upon detection of ammonia within the blood flow.

Optionally, the second dialysis module 200 can have one or more bubble filters 224, 226 in line with the dialysate circuit. The bubble filters 224, 226 can be in fluid communication with the dialysate such that presence of air bubbles within the dialysate is detected and communicated to the control unit 190 control unit 190. The control unit 190 is configurable to pause and/or power off the first dialysis module 100 upon detection of air bubbles within the dialysate.

The auxiliary electrolyte modules 220, 230 can be in line with the dialysate circuit of the second dialysis module 200. The auxiliary electrolyte modules 220, 230, can provide saline or solution into the dialysate flow. The auxiliary electrolyte modules 220, 230 can include sodium bicarbonate, and is optional, when the first dialysis module 100 is primed with a primer solution containing bicarbonate ($HCO_3^-$). For example, when the dialysate circuit is initially primed with a primer solution, typically containing saline (or half-normal saline) and bicarbonate ($HCO_3^-$), the need for a separate electrolyte reservoir can be obviated.

The bulkier and heavier second dialysis module 200 can be configured to remove urea. For example, the urea converter of the second dialysis module 200 can decompose urea removed from the blood stream into ammonia and carbon dioxide. The second dialysis module can remove the ammonia and vent the carbon dioxide to release the gas into the environment. The second dialysis module can include a plurality of types of sorbent materials configured to regenerate the dialysate. Due to the heavier nature of the second dialysis module, it can be tethered, stationary, and can receive a power source such as through a power cord to a wall outlet.

The combined system for hemodialysis including the mobile first dialysis module 100 connected to the second dialysis module 200 and the auxiliary module 180 can keep the P-BUTS low, at a non-toxic level, during a shortened stationary period On the other hand, other substances known to be toxic, such as phosphorus and urea can be removed from the blood in sufficient amounts in 6-10 hours, thus not requiring longer periods for a sufficient removal. Urea and phosphorus are not P-BUTS. These can be removed using the bulkier second dialysis module 200.

A patient can alternate use of the first dialysis module and a second dialysis module, for example for about 12 hours each during a 24 hour period, such that the patient remains mobile during the day while maintaining overall desired removal of toxins. This can be done, for example, over a combined cycle for removal of a variety of toxins between the first dialysis module and the second dialysis module.

Figure 3A:
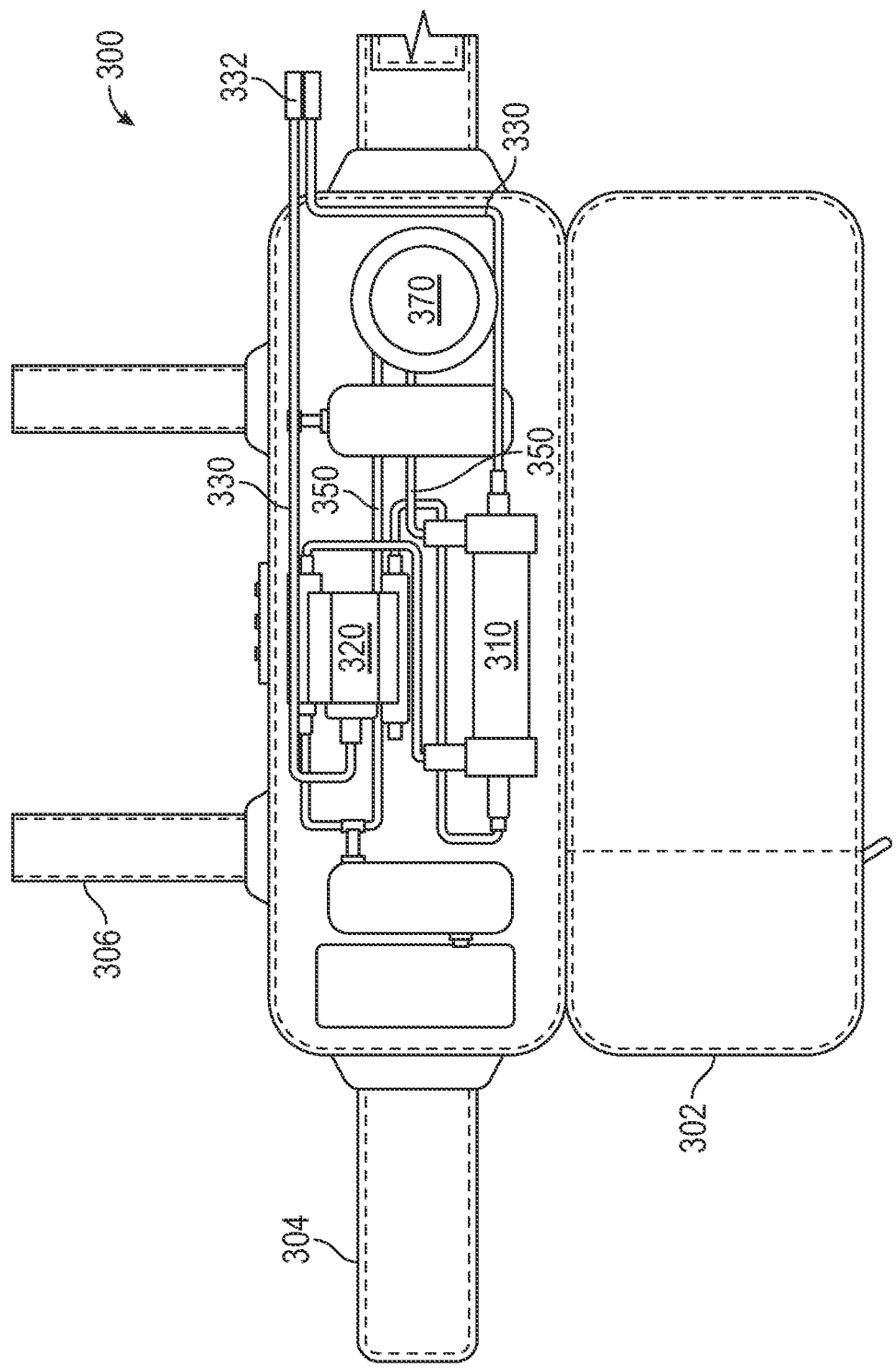
FIGS. 3A-3B are schematic diagrams of a portable daytime hemodialysis system with a detachable auxiliary pump module in an example.
Figure 3B:
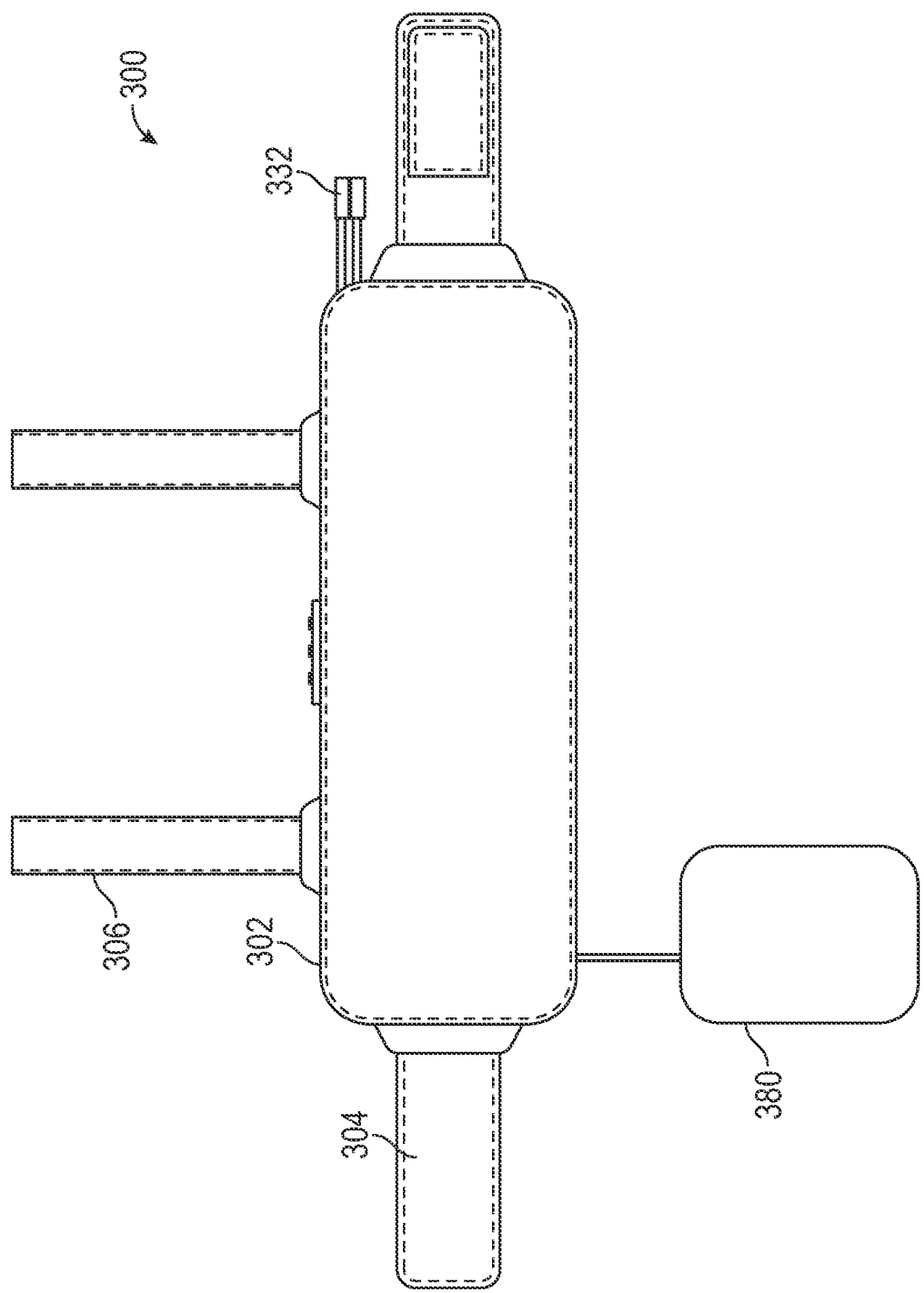

FIGS. 3A-3B are schematic diagrams of a portable daytime hemodialysis system 300 with a detachable auxiliary pump module 380 in an example. System 300 can be similar to, and contain similar components, to first dialysis module 100 discussed with reference to FIG. 1 above, except where otherwise noted.

System 300 can include an envelope 302, belt 304, suspenders 306, dialyzer 310, a pump 320, a blood circuit 330, a dialysate circuit 350, a sorbent 370, and ultrafiltrate module 380.

The envelope 302 can be an outer layer or skin on the system 300 that separates the components 310, 320, 330, 350, 370 from the outside environment. The envelope 302 can be sized or shaped to cover and conceal these components so that, to an outside observer, a patient wearing the system 300, is wearing a bag or box type item, not a full dialysis system. The envelope 302 can be waterproof or water resistant so as to allow the patient to wear the system 300 in an outside environment in a variety of weather, or to allow the patient to wear the system 300 in the shower. The envelope 302 can be sealed to prevent influx and outflux of water or components. The envelope 302 can optionally include a zipper or other opening mechanism to allow for maintenance of the system 300. Optionally, the system 300 can include a user interface on the outside of the envelope.

The belt 304 and the suspenders 306 can allow the patient to secure the system 300 to his or her body. The system 300 can be mounted on the belt 304. The belt 304 can allow for the system 300 to be worn on or near the waist or hips of the patient and adjusted to the patient waist size. The suspenders 306 can allow for additional security of the system 300 on the patient body, such as allowing the patient to situate the system 300 on their front, side, or back, as desired. The suspenders 306 can prevent gravity or patient movement throughout the day from dislodging the system 300. This can allow patient movement throughout the day.

The blood circuit 330 can be containing substantially within the envelope 302, with one or more connections 332 protruding out of the envelope, to allow connection to a patient circulatory system. For example, the connection 332 exiting the envelope 302 can include two connections, one for blood and one for dialysate, connected to a dual lumen catheter to allow for a single point for attachment to the patient circulatory system.

The dialysate circuit 350, the sorbent 370, the dialyzer 310, and the pump 320 can all reside within the envelope 302. When the patient desires to use a connecting stationary system, such as second dialysis module 200 discussed above, the patient can open the envelope, such as by a zipper, and attach the dialysate circuit 350 into the nighttime system.

The ultrafiltrate module 380 can be separate from the rest of the system 300, such as outside the envelope 302. The ultrafiltrate module 380 can be an auxiliary module to the system 300 and can be easily detachable or connectable to the system 300 when the patient desires fluid removal. The ultrafiltrate module 380 can be, for example, a separate pouch, bag, envelope, or case, holding an ultrafiltrate collector, corresponding pump, and connection for attachment to the envelope 302, such as auxiliary module 180 described with reference to first dialysis module 100 earlier. The ultrafiltrate module 380 can, for example, be attached our mounted on the patient's body, such as on his or her leg or chest, when in use, and attached through a connection to the envelope 302. If the ultrafiltrate module 380 is worn by the patient, the patient can continue his or her normal mobility while fluid removal is occurring.

In some cases, the ultrafiltrate module 380 can be stationary, or on or near a surface, such as a table, when the patient hooks into the ultrafiltrate module 380. The patient can know when to use the ultrafiltrate module 380 for removal of fluid such as by the patient's change in weight throughout the day, and through careful planning with his or her doctor. If the ultrafiltrate module 380 is used while the patient is stationary, the patient can then detach from the ultrafiltrate module 380 after fluid removal is done and resume his or her normal mobility with just the envelope 302.

Figure 4A:
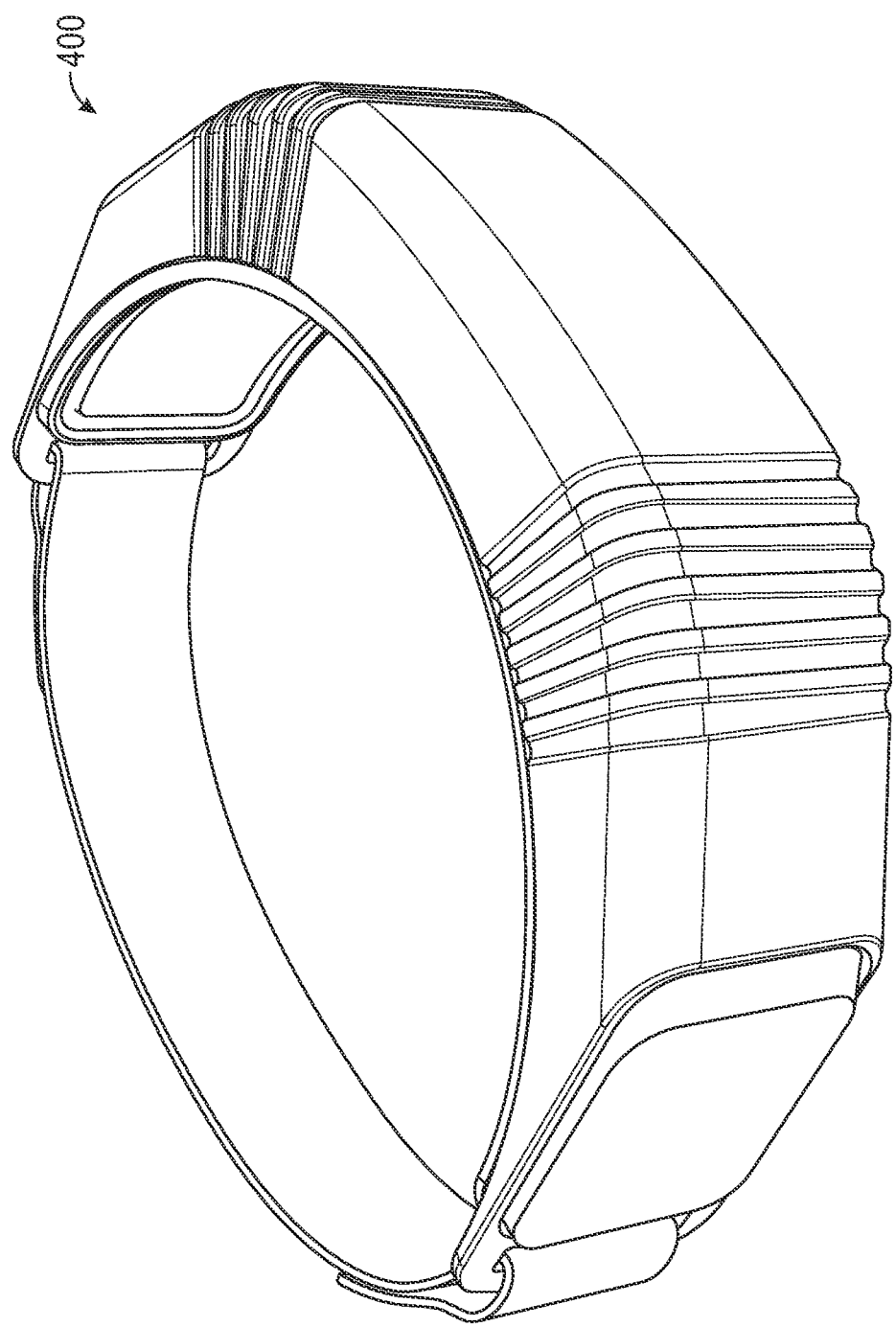
Figure 4B:
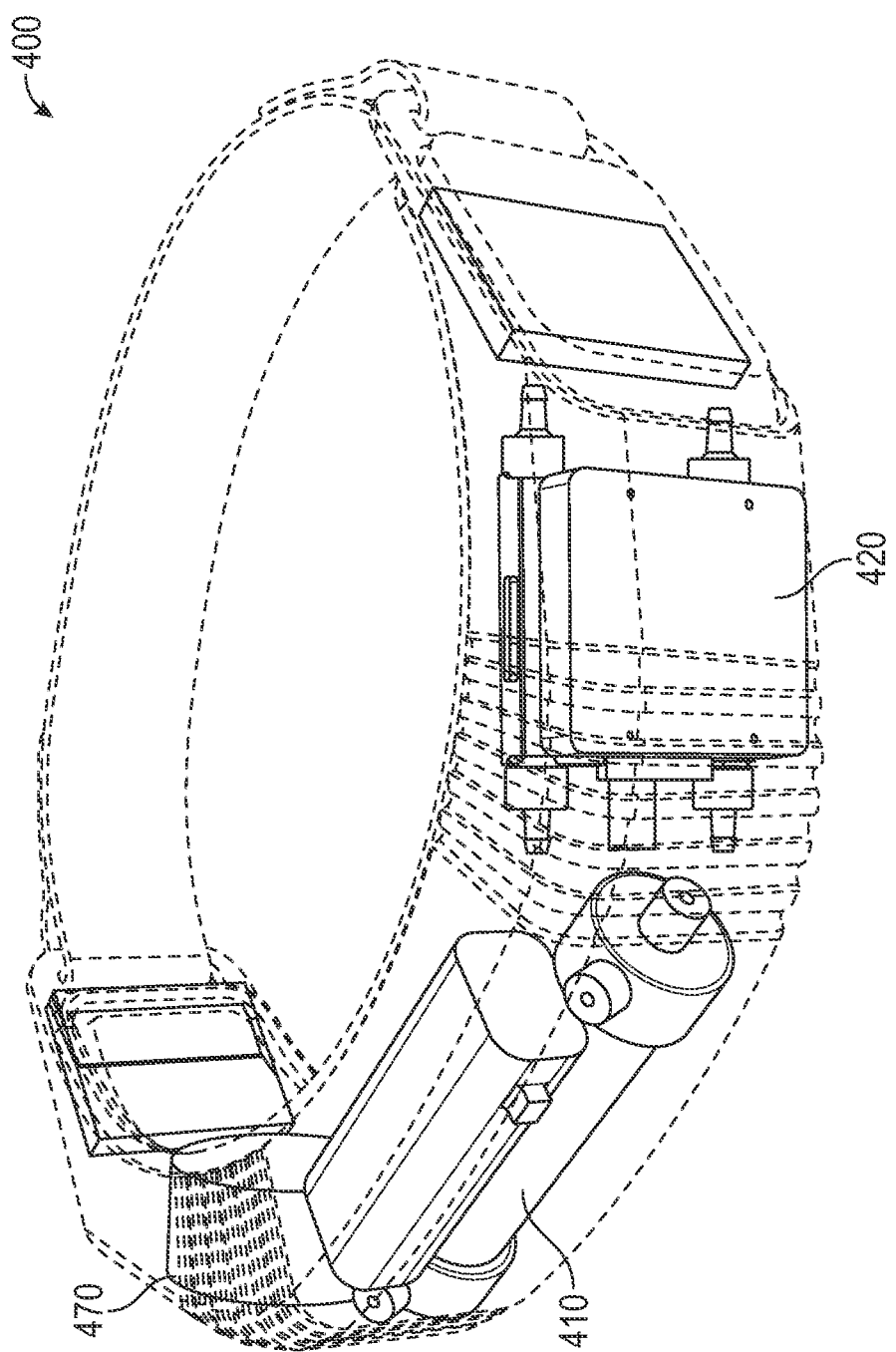

FIGS. 4A-4C are perspective views of a portable daytime hemodialysis system 400 in an example. System 400 can have components similar to those in first dialysis module 100 discussed above, except where otherwise noted. System 400 can include a casing 402, belt 404, dialyzer 410, a pump 420, a blood circuit, a dialysate circuit, and a sorbent 470.

The belt 404 of system 400 can allow for mounting of the components such as dialyzer 410, pump 420, blood circuit, dialysate circuit, and sorbent 470, within the casing 402. In system 400, the components can be mounted in the front of the belt so that the patient can wear them on his or her front side as shown in FIG. 4C. This can allow for the patient to easily hook the system 400 into his or her bloodstream.

Figure 5A:
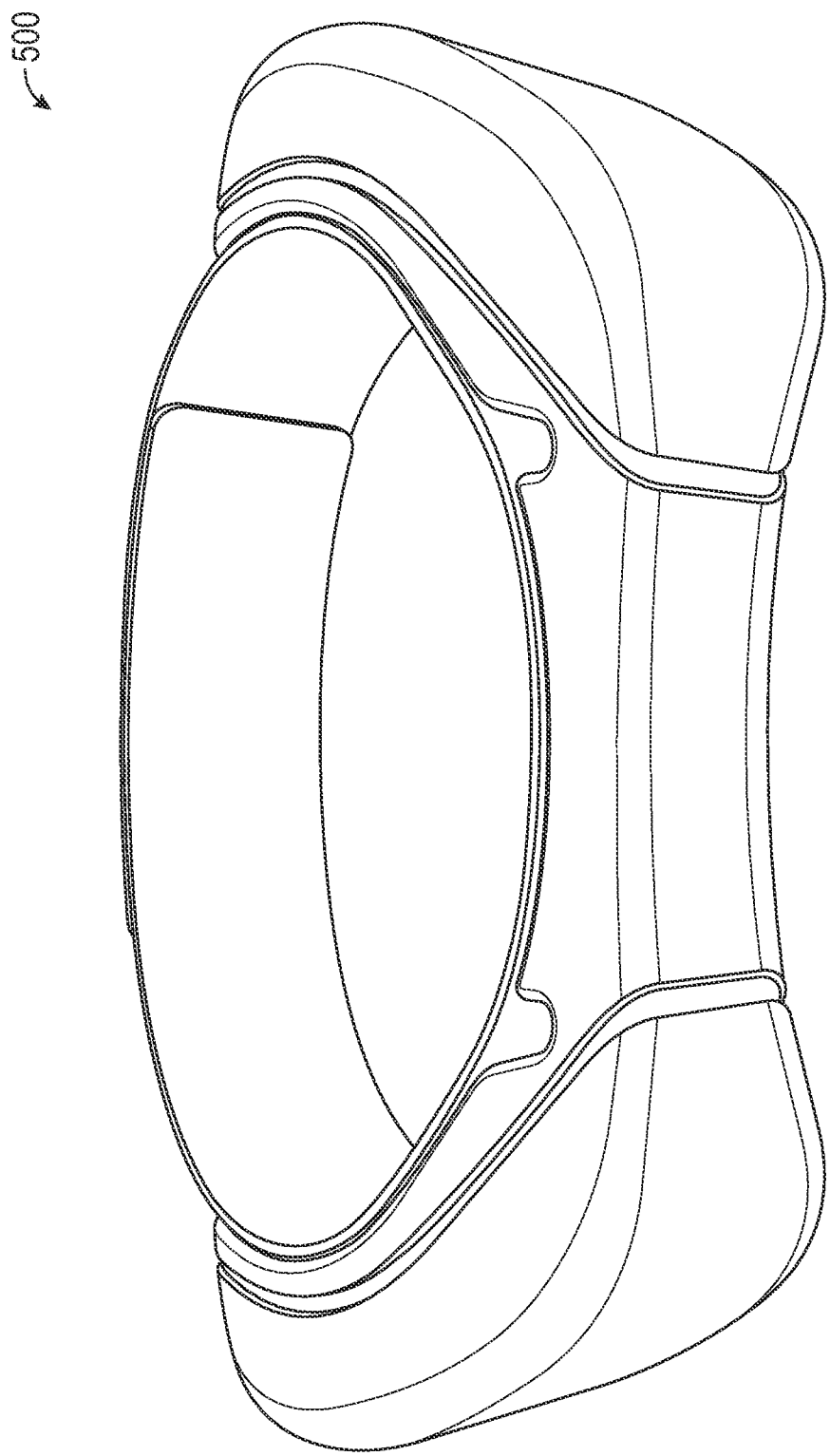
Figure 5B:
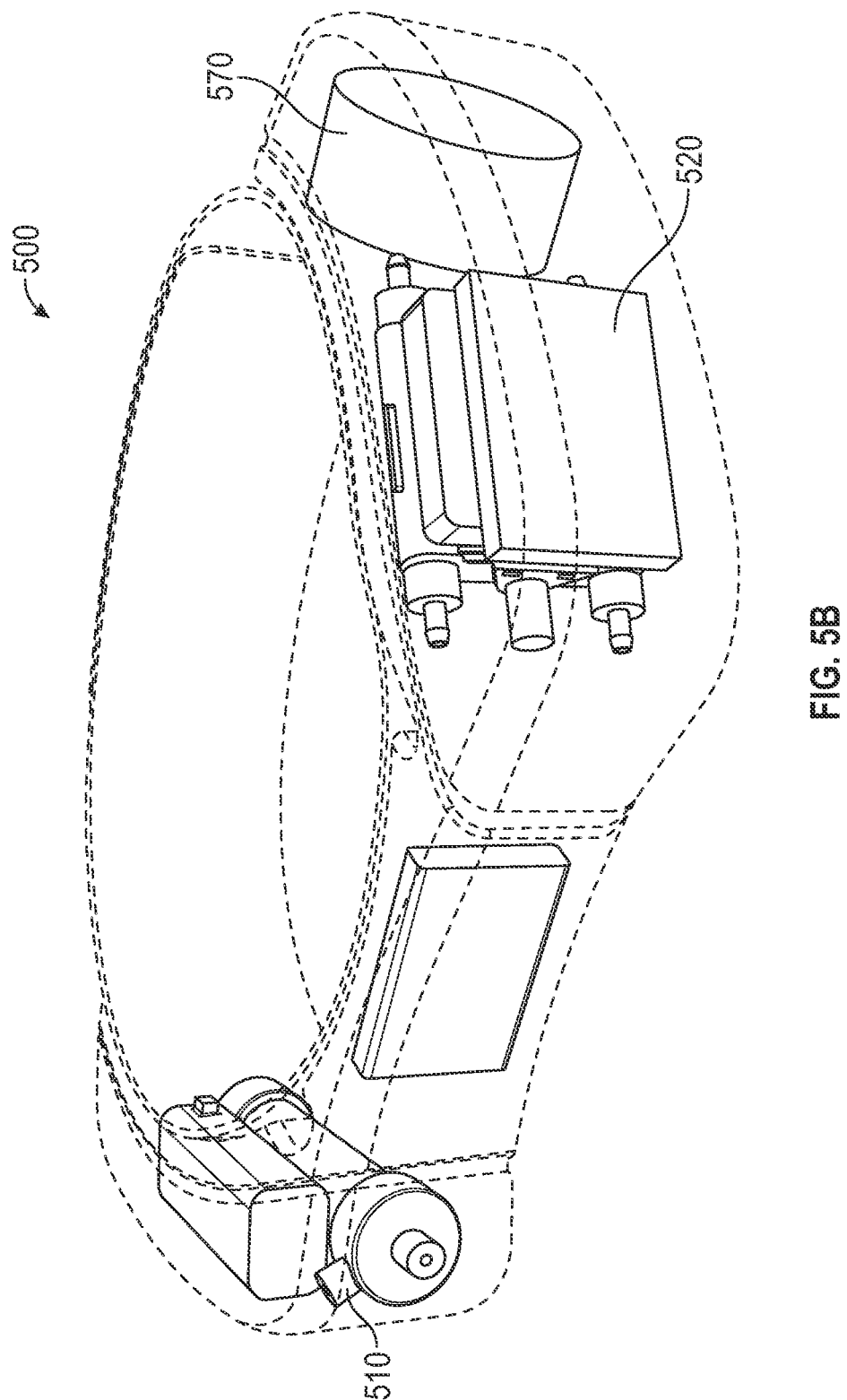

FIGS. 5A-5C are perspective views of a portable daytime hemodialysis system 500 in an example. System 500 can have components similar to those in first dialysis module 100 discussed above, except where otherwise noted. System 500 can include a casing 502, belt 504, dialyzer 510, a pump 520, a blood circuit, a dialysate circuit, and a sorbent 570.

The casing 502 on the belt 504 is situated so that the components are spread out between a patient's sides or hips. This can allow for wearing of system 500 without a protrusion at the patient's belly. This can allow for more mobility of the patient when bending.

Figure 6:
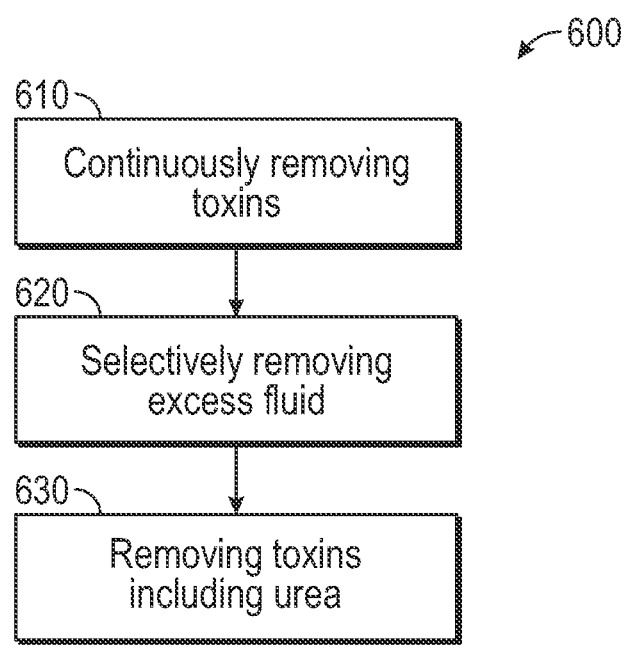
FIG. 6 is a flow chart depicting a method of using a hemodialysis system in an example.

FIG. 6 is a flow chart depicting a method 600 of using a hemodialysis system in an example. Method 600 can include steps 610 to 630. Step 610 can include continuously removing toxins from blood with a portable dialysis module situated on the patient's body. This can be is done, for example, over a first time period during a time when the patient is mobile, such as during the daytime. Step 620 can include selectively removing excess fluid from the portable dialysis module by connecting the portable dialysis module to a detachable auxiliary module comprising an ultrafiltrate collector. This can be done at particular times throughout the patient's day.

Step 630 can include removing toxins, including urea, from the blood with a stationary dialysis module comprising the portable dialysis module and one or more sorbents connectable thereto. Removing toxins, including urea, from the blood with a stationary dialysis module can be done over a second time period comprising a time when the patient is stationary, such as at nighttime.

As used herein, and unless otherwise specified, the term "about" or "approximately" means an acceptable error for a particular value as determined by one of ordinary skill in the art, which depends in part on how the value is measured or determined. In certain examples, the term "about" or "approximately" means within 1, 2, 3, or 4 standard deviations. In certain examples, the term "about" or "approximately" means within 30%, 25%, 20%, 15%, 10%, 9%, 8%, 7%, 6%, 5%, 4%, 3%, 2%, 1%, 0.5%, 0.1%, or 0.05% of a given value or range. In certain examples, the term "about" or "approximately" means within 40.0 mm, 30.0 mm, 20.0 mm, 10.0 mm 5.0 mm 1.0 mm, 0.9 mm, 0.8 mm, 0.7 mm, 0.6 mm, 0.5 mm, 0.4 mm, 0.3 mm, 0.2 mm or 0.1 mm of a given value or range. In certain examples, the term "about" or "approximately" means within 1 hour, within 45 minutes, within 30 minutes, within 25 minutes, within 20 minutes, within 15 minutes, within 10 minutes, within 5 minutes, within 4 minutes, within 3 minutes within 2 minutes, or within 1 minute. In certain examples, the term "about" or "approximately" means within 20.0 degrees, 15.0 degrees, 10.0 degrees, 9.0 degrees, 8.0 degrees, 7.0 degrees, 6.0 degrees, 5.0 degrees, 4.0 degrees, 3.0 degrees, 2.0 degrees, 1.0 degrees, 0.9 degrees, 0.8 degrees, 0.7 degrees, 0.6 degrees, 0.5 degrees, 0.4 degrees, 0.3 degrees, 0.2 degrees, 0.1 degrees, 0.09 degrees, 0.08 degrees, 0.07 degrees, 0.06 degrees, 0.05 degrees, 0.04 degrees, 0.03 degrees, 0.02 degrees or 0.01 degrees of a given value or range.

As used herein, the terms "connected", "operationally connected", "coupled", "operationally coupled", "operationally linked", "operably connected", "operably coupled", "operably linked," and like terms, refer to a relationship (mechanical, linkage, coupling, etc.) between elements whereby operation of one element results in a corresponding, following, or simultaneous operation or actuation of a second element. It is noted that in using said terms to describe inventive examples, specific structures or mechanisms that link or couple the elements are typically described. However, unless otherwise specifically stated, when one of said terms is used, the term indicates that the actual linkage or coupling may take a variety of forms, which in certain instances will be readily apparent to a person of ordinary skill in the relevant technology.

As used herein, the terms "comprises", "comprising", or any other variation thereof, are intended to cover a nonexclusive inclusion, such that a process, method, article, or apparatus that comprises a list of elements does not include only those elements but may include other elements not expressly listed or inherent to such process, method, article, or apparatus.

As used herein, the term "mobile," can mean ambulatory, untethered to a stationary object, a device with self-contained power, a lightweight device, and a wearable device, a device that can be worn during a typical day without causing excessive user fatigue due to weight.

As used herein, the terms "user", "subject" or "patient" are used interchangeably. As used herein, the terms "subject" and "subjects" refers to an animal (e.g., birds, reptiles, and mammals), preferably a mammal including a primate (e.g., a monkey, chimpanzee, and a human) and a non-primate (e.g., a camel, donkey, zebra, cow, pig, horse, cat, dog, rat, and mouse). In certain examples, the mammal is 0 to 6 months old, 6 to 12 months old, 1 to 5 years old, 5 to 10 years old, 10 to 15 years old, 15 to 20 years old, 20 to 25 years old, 25 to 30 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old, 95 to 100 years old, or 100 to 120 years old.

VARIOUS NOTES & EXAMPLES

Each of these non-limiting examples can stand on its own or can be combined in various permutations or combinations with one or more of the other examples.

Example 1 can include a system for hemodialysis can include a first dialysis module and an auxiliary module detachably connectable to the first dialysis module. The first dialysis module can include a dialyzer, a blood circuit configured to receive blood from a patient, circulate the blood through the dialyzer, and return cleaned blood to the patient, a dialysate circuit configured to circulate dialysate through the dialyzer and remove impurities from the blood and a first sorbent for removing toxins from the blood. The auxiliary module can include a pump connectable to the dialyzer for pumping the dialysate through the dialysate circuit and a filter configured to remove fluid from the system, the filter fluidly coupled to the pump and the dialysate circuit.

Example 2 can include Example 1, wherein the first dialysis module is mounted on a belt such that the patient can wear the first dialysis module during daytime, and wherein the patient is mobile and untethered.

Example 3 can include any of Examples 1-2, wherein the first sorbent comprises activated carbon for continuously removing the free fraction of protein bound uremic toxins.

Example 4 can include any of Examples 1-3, further comprising a second dialysis module detachably connectable to the first dialysis module, the second dialysis module including one or more hook-ups for connecting to the first dialysate module and a second sorbent for removing toxins from the blood.

Example 5 can include any of Examples 1-4, wherein the second sorbent comprises urease for removing urea from blood.

Example 6 can include any of Examples 1-5, wherein the second dialysis module further comprises a power cord for connection to an electrical outlet.

Example 7 can include any of Examples 1-6, wherein the dialyzer comprises a side-by-side pulsatile pump fluidly coupled to the blood circuit and the dialysate circuit, the pump configured to simultaneously drive blood and dialysate through the dialyzer.

Example 8 can include any of Examples 1-7, further comprising a flow sensor fluidly coupled to one of the dialysate circuit and the blood circuit, the flow sensor configured to detect flow of fluid therethrough.

Example 9 can include any of Examples 1-8, further comprising an envelope at least partially enclosing the first dialysis module, wherein the envelope is waterproof.

Example 10 can include any of Examples 1-9, wherein the envelope comprises a double layer material.

Example 11 can include any of Examples 1-10, wherein the envelope further comprises a zipper configured to allow insertion and removal of the first dialysis module.

Example 12 can include any of Examples 1-11, wherein the envelope further comprises a connector element for connecting the auxiliary module to the first dialysis module.

Example 13 can include any of Examples 1-12, wherein the auxiliary module further includes a pump connectable to the dialyzer for pumping the dialysate through the dialysate circuit; and a filter configured to remove fluid from the system, the filter fluidly coupled to the pump and the dialysate circuit.

Example 14 can include any of Examples 1-13, further comprising an inlet for a dual lumen catheter for fluid connection to the dialyzer.

Example 15 can include any of Examples 1-14, wherein the first dialysis module further comprises a battery.

Example 16 can include any of Examples 1-15, wherein the first dialysis module and the second dialysis module are configured to be used in an alternating fashion over a combined cycle to provide hemodialysis to a patient.

Example 17 can include a method of hemodialysis including continuously removing toxins from blood with a portable dialysis module situated on the patient's body and selectively removing excess fluid from the portable dialysis module by connecting the portable dialysis module to a detachable auxiliary module comprising an ultrafiltrate collector.

Example 18 can include Example 17, wherein continuously removing toxins from blood with a portable dialysis module is performed over a first time period comprising a time when the patient is mobile.

Example 19 can include any of Examples 17-18, further comprising removing toxins, including urea, from the blood with a stationary dialysis module comprising the portable dialysis module and one or more sorbents connectable thereto.

Example 20 can include any of Examples 17-19, wherein removing toxins, including urea, from the blood with a stationary dialysis module is performed over a second time period comprising a time when the patient is stationary.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific examples in which the invention can be practiced. These examples are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed example. Thus, the following claims are hereby incorporated into the Detailed Description as examples or examples, with each claim standing on its own as a separate example, and it is contemplated that such examples can be combined with each other in various combinations or permutations. The scope of the invention should be determined with reference to the appended claims, along with the full scope of equivalents to which such claims are entitled.

What is claimed is:

1. A system for hemodialysis comprising:
    a first dialysis module comprising:
        a dialyzer;
        a blood circuit configured to receive blood from a patient, circulate the blood through the dialyzer, and return cleaned blood to the patient;
        a dialysate circuit configured to circulate dialysate through the dialyzer and remove impurities from the blood;
        a first sorbent for removing toxins from the blood; and
        a first case enclosing the dialyzer, the blood circuit, the dialysate circuit and the first sorbent;
    an auxiliary module detachably connectable to the first dialysis module, the auxiliary module comprising:
        an ultrafiltrate collector operably couplable to the dialysate circuit for removing excess fluid therefrom;
        an ultrafiltrate pump; and
        a second case enclosing the ultrafiltrate collector and the ultrafiltrate pump;
    a fluid line extending through the first case and the second case to connect the ultrafiltrate pump and the dialysate circuit; and
    a connector element disposed in the fluid line to allow a user to release the auxiliary module from the first dialysis module without interrupting flow in the dialysate circuit.

2. The system of claim 1, wherein the first dialysis module is mounted on a belt such that the patient can wear the first dialysis module during daytime, and wherein the patient is mobile and untethered.

3. The system of claim 1, wherein the first sorbent comprises activated carbon for continuously removing a free fraction of protein bound uremic toxins.

4. The system of claim 1, wherein the dialyzer comprises a side-by-side pulsatile pump fluidly coupled to the blood circuit and the dialysate circuit, the side-by-side pulsatile pump configured to simultaneously drive blood and dialysate through the dialyzer.

5. The system of claim 1, further comprising a flow sensor fluidly coupled to one of the dialysate circuit and the blood circuit, the flow sensor configured to detect flow of fluid therethrough.

6. The system of claim 1, wherein the first case comprises an envelope at least partially enclosing the first dialysis module, wherein the envelope includes a user interface for the first dialysis module that is operable from outside of the envelope and first and second couplers for connecting the blood circuit to the patient and the auxiliary module is positioned outside of the envelope.

7. The system of claim 6, wherein the envelope is waterproof and comprises a double layer material.

8. The system of claim 7, wherein the envelope further comprises a zipper configured to allow insertion and removal of the first dialysis module.

9. The system of claim 6, wherein the envelope further comprises the connector element for connecting the auxiliary module to the first dialysis module.

10. The system of claim 1, wherein the auxiliary module further comprises:
    a filter configured to remove fluid from the system, the filter fluidly coupled to the ultrafiltrate pump and the dialysate circuit.

11. The system of claim 1, further comprising an inlet for a dual lumen catheter for fluid connection to the dialyzer.

12. The system of claim 4, wherein the first dialysis module further comprises a battery to power the side-by-side pulsatile pump.

13. The system of claim 12, further comprising a second dialysis module detachably connectable to the first dialysis module on opposite sides of the first sorbent, the second dialysis module comprising:
    one or more hook-ups for connecting to the first dialysis module, wherein each of the one or more hook-ups is located in the first case; and
    a second sorbent for removing toxins from the blood;
    wherein the second dialysis module can be attached to the dialysate circuit to bypass the first sorbent.

14. The system of claim 13, wherein the second sorbent comprises urease for removing urea from blood.

15. The system of claim 13, wherein the second dialysis module further comprises a power cord for connection to an electrical outlet to power a side-by-side pulsatile pump alternatively with a battery.

16. The system of claim 13, wherein the first dialysis module and the second dialysis module are configured to be used in an alternating fashion over a combined cycle to provide hemodialysis to a patient such that the first sorbent and the second sorbent are used alternatively.

17. A system for hemodialysis comprising:
a first dialysis module comprising:
   a dialyzer;
   a blood circuit configured to receive blood from a patient, circulate the blood through the dialyzer, and return cleaned blood to the patient;
   a dialysate circuit configured to circulate dialysate through the dialyzer and remove impurities from the blood;
   a first sorbent for removing toxins from the blood; and
   an envelope enclosing the dialyzer, the blood circuit, the dialysate circuit and the first sorbent, wherein the envelope comprises an outer layer of skin sized and shaped to cover and conceal the first dialysis module;
   an opening mechanism to allow access to an interior of the envelope;
   a user interface for the first dialysis module that is operable from outside of the envelope; and
   at least one of a belt and a pair of suspenders connected to the envelope; and
an auxiliary module detachably connectable to the first dialysis module, the auxiliary module comprising:
   an ultrafiltrate collector operably couplable to the dialysate circuit for removing excess fluid therefrom;
wherein the auxiliary module is located outside the envelope.

18. A system for hemodialysis comprising:
a first dialysis module comprising:
   a dialyzer;
   a blood circuit configured to receive blood from a patient, circulate the blood through the dialyzer, and return cleaned blood to the patient;
   a dialysate circuit configured to circulate dialysate through a loop including the dialyzer to remove impurities from the blood;
   a first sorbent in the dialysate circuit for removing toxins from the blood;
   a pump for the blood circuit and the dialysate circuit; and
   a battery for supplying power to the pump;
an auxiliary module detachably connectable to the first dialysis module, the auxiliary module comprising an ultrafiltrate collector operably couplable to the dialysate circuit for removing excess fluid therefrom, wherein the auxiliary module can be disconnected form the dialysate circuit without disrupting flow through the loop; and
a second dialysis module detachably connectable to the first dialysis module, the second dialysis module comprising:
   a power cord for supplying power to the pump alternatively with the battery;
   one or more hook-ups for connecting to the dialysate circuit so that the loop is expanded and bypasses the first sorbent; and
   a second sorbent for removing toxins from the blood.

19. The system of claim 18, further comprising an envelope at least partially enclosing the first dialysis module, wherein the auxiliary module and the second dialysis module are positioned outside of the envelope.

* * * * *